US006905860B2

(12) United States Patent
Ishikawa et al.

(10) Patent No.: US 6,905,860 B2
(45) Date of Patent: Jun. 14, 2005

(54) ARTIFICIAL CHROMOSOME

(75) Inventors: Fuyuki Ishikawa, Kanagawa (JP); Mamoru Hasegawa, Ibaraki (JP)

(73) Assignee: DNAVEC Research Inc., Ibaraki (JP)

(*) Notice: Subject to any disclaimer, the term of this patent is extended or adjusted under 35 U.S.C. 154(b) by 0 days.

(21) Appl. No.: 10/780,464

(22) Filed: Feb. 17, 2004

(65) Prior Publication Data

US 2004/0219634 A1 Nov. 4, 2004

Related U.S. Application Data

(62) Division of application No. 09/254,947, filed as application No. PCT/JP97/03305 on Sep. 18, 1997, now Pat. No. 6,716,608.

(30) Foreign Application Priority Data

Sep. 18, 1996 (JP) .............................................. 8-246749

(51) Int. Cl.⁷ ............................ C12N 9/12; C12N 1/14; C12P 21/06; A61K 35/78; C07H 21/02
(52) U.S. Cl. ................ 435/194; 435/254.2; 435/254.21; 435/69.1; 536/23.1; 530/370; 530/387.3; 530/388.21
(58) Field of Search .............................. 435/194, 254.2, 435/254.21, 69.1; 530/370, 387.3, 388.21; 536/23.1

(56) References Cited

FOREIGN PATENT DOCUMENTS

| CA | 2263823 | 3/1998 |
|---|---|---|
| WO | WO 98/08964 | 3/1998 |

OTHER PUBLICATIONS

Autexier et al., "Functional Reconstitution Of Wild–Type And Mutant *Tetrahymena* Telomerase," *Genes & Development* 8:563–575 (1994).

Autexier et al., "Reconstitution Of Human Telomerase Activity And Identification Of A Minimal Functional Region Of the Human Telomerase RNA," *The EMBO Journal* 15(21):5928–5935 (1996).

Brem et al., "YAC Transgenesis In Farm Animals: Rescue Of Albinism In Rabbits," *Molecular Reproduction And Development* 44:56–62 (1996).

Davies et al., "YAC Transfer Into Mammalian Cells By Cells Fusion," *Methods in Molecular Biology* 54:281–292 (1996).

Gobin et al., "Transfer Of Yeast Artificial Chromosomes Into Mammalian Cells And Comparative Study Of Their Integrity," *Gene* 163:27–33 (1995).

Gnirke et al., "Microinjection Of Intact 200– to 500–kb Fragments Of YAC DNA Into Mammalian Cells," *Genomics* 15:659–667 (1993).

Grady et al., "Highly Conserved Repetitive DNA Sequences Are Present At Human Centromeres," *Proc. Natl. Acad. Sci. USA* 89:1695–1699 (1992).

Harrington et al., "Formation of De Novo Centromers and Construction Of First–Generation Human Artificial Microchromosomers," *Nature Genetics*, 15:345–354 (1997).

Hayatsu et al., "A Modified *S. cerevisiae* Telomerase That Synthesizes The Human Telomeric Repeats In Vivo," *Cell Structure and Function* (Abstract IP–03), 21:582 (1996).

Henning K. et al., "Humanizing The Yeast Telomerase Template," *Proc. Natl. Acad. Sci. U.S.A.*, 95:5667–5671 (1998).

Hodgson et al., "Human Huntingtin Derived From YAC Transgenes Compensates For Loss Of Murine Huntingtin By Rescue Of The Embryonic Lethal Phenotype," *Human Molecular Genetics* 5(12):1875–1885 (1996).

Huxley, "Mammalian Artificial Chromosomes: A New Tool For Gene Therapy," *Gene Therapy* 1:7–12 (1994).

Huxley, "Mammalian Artificial Chromosomes and Chromosomes Transgenics," *Trends Genet.* 13:345–347 (1997).

Huxley et al., "The Human HPRT Gene On A Yeast Artificial Chromosome Is Functional When Transferred To Mouse Cells By Cell Fusion," *Genomics* 9:742–750 (1991).

Ikeno et al., "Distribution of CENP–B Boxes Reflected In CREST Centromere Antigenic Sites On Long–Range Alpha– Satellite DNA Arrays Of Human Chromosome 21," *Hum. Mol. Genet.* 3:1245–1257 (1994).

McEachern et al., "Runaway Telomere Elongation Caused By Telomerase RNA Mutations," *Nature* 376:403–409 (1995).

McEachern et al, "Runaway Telomere Elongation Caused By Telomerase RNA Gene Mutations," *GenBank Accession Number* U31465; Aug. 31, 1995.

Moyzis, "A Highly Conserved Repetitive DNA Sequence, (TTAGGG)n, Present At The Telomeres Of Human Chromosomes," *Proc. Natl. Acad. Sci.* 85 (1988).

Peterson et al., "Use Of Yeast Artificial Chromosomes (YACs) For Studying Control Of Gene Expression: Correct Regulation Of The Genes Of A Human β–globin Locus YAC Following Transfer To Mouse Erythroleukemia Cell Lines," *Proc. Natl. Acad. Sci. USA* 90:11207–11211 (1993).

Riley et al., "Targeted Integration Of Neomycin Into Yeast Artifical Chromosomes (YACs) For Transfection Into Mammalian Cells," *Nucleic Acids Research* 20(12):2971–2976 (1992).

(Continued)

*Primary Examiner*—Rebecca E. Prouty
*Assistant Examiner*—Malgorzata A. Walicka
(74) *Attorney, Agent, or Firm*—Clark & Elbing LLP

(57) ABSTRACT

An artificial mammalian chromosome, more specifically, a clone containing a mammalian centromere sequence and a DNA replication origin with mammalian telomere sequences added to both ends of the clone, is provided by preparing a CEPH artificial yeast chromosome library containing a human genome, identifying clones having a repetitive human alphoid sequence from this library, and further preparing a yeast strain in which mammalian telomere sequences are added to the ends of its chromosome.

6 Claims, No Drawings

OTHER PUBLICATIONS

Schedl et al., "A Method For the Generation Of YAC Transgenic Mice By Pronuclear Microinjection," *Nucleic Acids Research* 21(20):4783–4787 (1993).

Singer et al., "TLC1:Template RNA Component Of *Saccharomyces cerevisiae* Telomerase," *Science,* 266:404–409 (1994).

Sun et al., "Engineering A Mini–herpesvirus As A General Strategy To Transduce Up To 180 kb Of Functional Self–replicating Human Mini–chromosomes," *Gene Therapy* 3:1081–1088 (1996).

Taylor et al., "Addition Of Functional Human Telomeres To YACs," *Human Molecular Genetics* 3(8):1383–1386 (1994).

Vocero–Akbani et al., "Mapping Human Telomere Regions With YAC and P1 Clones: Chromosome–Specific Markers For 27 Telomeres Including 149 STSs and 24 Polymorphisms For 14 Proterminal Regions," *Genomics* 36:492–506 (1996).

Yu et al., "In Vivo Alteration Of Telomer Sequences and Senescence Caused By Mutated Tetrahymena Telomerase RNAs," *Nature,* 344:126–132 (1990).

ARTIFICIAL CHROMOSOME

CROSS REFERENCE TO RELATED APPLICATIONS

This application is a divisional of U.S. application Ser. No. 09/254,947, now U.S. Pat. No. 6,716,608, filed Mar. 13, 2000, which is the U.S. national stage of international application number PCT/JP97/03305, filed Sep. 18, 1997, which, in turn, claims the benefit of Japanese application number 8/246749, filed Sep. 18, 1996.

TECHNICAL FIELD

The present invention relates to the field of genetic engineering, more specifically, it relates to an artificial mammalian chromosome prepared by genetic engineering techniques.

BACKGROUND ART

Various methods of treating diseases attributed to an inherited or an acquired genetic defect, namely a genetic disease, have been developed. Gene therapy is one such method for treating a genetic disorder fundamentally by replacing a defective gene with a normal gene or complementing a normal gene.

At present, the most clinically and fundamentally developed method of introducing a gene comprises linking a short DNA fragment like cDNA to a downstream site of an ectopic enhancer or promoter that originally does not exist upstream of the gene, introducing the resulting DNA fragment into a cell using a virus or liposome, and allowing the cell to express the gene. This method is easy to manipulate because a short DNA fragment is used. Furthermore, it has a relatively high success rate of introducing a gene into a cell. However, there are some disadvantages. First, it is difficult to control the expression of an introduced gene. In this method, the expression control of a desired gene in a human in vivo is difficult because the promoter and enhancer used are derived from viruses. Second, the existing pattern of an introduced gene in a cell is not stable. Untargeted genes may be destroyed or an excessive number of introduced genes may exist. This is because the introduced gene in a cell may be randomly integrated into a chromosomal DNA. Alternatively, the introduced gene may independently exist extrachromosomally and be maintained without being controlled by DNA synthesis during the S phase or chromosome separation during the M phase of a cell. This fact makes it difficult to control expression of a therapeutic gene in gene therapy and to exhibit therapeutic effects continuously.

For example, sickle cell anemia and thalassemia drew the most attention in the early 1980s as targets for gene therapy. In spite of numerous patients with these diseases, it is not being studied much at present because it is difficult to strictly control the expression of the therapeutic gene (a globin gene) to be introduced. Furthermore, since processing of a huge DNA molecule like a globin gene using restriction enzymes is limited, homologous recombination using yeast is more effective than recombination using an E. coli plasmid. A stable chromosome can thus be prepared in a yeast cell. If such a chromosome is capable of replicating in a human cell, it can be used for the most ideal gene therapy. In the field of gene therapy, it is essential to develop a vector system in which a human gene with an expression control region can function and be stably maintained in a human cell.

An "artificial chromosome" that is a yeast artificial chromosome (YAC) vector has been developed. A long-chain DNA molecule such as a gene ligated to a promoter region and/or an enhancer region can be introduced into this vector and stably maintained following the mechanisms of DNA replication and separation in yeast. A DNA fragment requires three functional structures, a centromere, a DNA replication origin, and a telomere, to function as a chromosome. Based on this fact, the YAC vector has been constructed to contain genes for these three functional structures.

However, the above yeast functional structures do not function in mammals, including humans. Therefore, the functional structures from a mammal or those modified to a mammalian type structure must be used to constitute an artificial chromosome that functions in a mammalian cell.

A centromere, a DNA replication origin, and a telomere of yeast each consist of a several kb DNA sequence whose functions have been well analyzed. In contrast, a centromere of a mammal, especially of a human, is a huge DNA molecule in which a repetitive sequence called the alphoid sequence repeats over several hundred kb or more. In addition, even the primary structure of a mammalian DNA replication origin has not been clarified. Thus, the analysis of functional structures in a mammal is far behind that in yeast, and an artificial mammalian chromosome has yet to be constructed.

Mammals, including humans, commonly have a 5'-TTAGGG-3' sequence as a repetitive unit of a telomere sequence.

DISCLOSURE OF THE INVENTION

An objective of the invention is to provide an artificial mammalian type chromosome, more specifically, an artificial chromosome having a mammalian type telomere sequence added to both its ends. The current invention provides a yeast strain capable of having a mammalian type telomere sequence connected to both ends of its chromosome.

A chromosome requires minimum functional structures of three elements to function. The first is a DNA replication origin region that ensures a single DNA replication during the S phase following mitosis. The second is a centromere that ensures the correct separation of each set of replicated DNA into daughter cells. The third is a telomere that caps the ends of linear chromosomes to ensure their stable existence in a nucleus.

It is evident that a centromere sequence of a mammal, especially of a human, is a huge DNA molecule containing a specific DNA sequence called the repetitive alphoid sequence that repeats over a few hundred kilo base pairs in tandem (M. Ikeno, H. Masumoto & T. Okazaki, Hum Mol Genet 3: 1245–1257 (1994)). Such a huge DNA molecule cannot be manipulated by means of conventional recombinant DNA techniques. Therefore, the present inventors employed a CEPH artificial yeast chromosome library containing a human genome inserted into a yeast YAC vector into which a long DNA molecule can be inserted. Clones containing the repetitive human alphoid sequence were identified from this library to serve as the basis of an artificial mammalian chromosome. The primary structure of a DNA replication origin in a human genome has not been identified, however, it is estimated that one DNA replication origin exists on average in each 100 kb of a human genome DNA (Molecular biology of cell, third edition, Kyoikusha). Therefore, a YAC clone containing the above-described repetitive alphoid sequence is thought to contain a DNA replication origin.

However, the YAC clone itself does not function as an artificial mammalian chromosome due to the lack of a telomere sequence. Thus, the present inventors engaged in searching for a method of adding a mammalian telomere sequence to the ends of DNA of the thus-obtained YAC clone.

Specifically, the present inventors engaged in investigating a method for adding a telomere sequence not in vitro but in vivo (in yeast), in other words, a method for preparing a yeast strain in which a mammalian telomere sequence can be added to a yeast genome, considering that a desired artificial chromosome is a long-chain DNA molecule and is easily damaged and physically decomposed by nonspecific enzymes.

A telomerase consists of a protein component and an RNA component as a template for extending the telomere sequence. The telomere sequence is added to a chromosome as a complementary sequence to the template RNA. The present inventors modified a template RNA encoding a yeast telomere sequence $(TG_{1-3})_n$, so as to encode a mammalian telomere sequence $(TTAGGG)_n$, by in vitro mutagenesis, cloned the modified template RNA in an expression plasmid, then introduced the plasmid into yeast. A hybrid telomerase (composed of a mammalian template RNA derived from the plasmid and protein derived from host yeast) was constructed in yeast. Thus, a yeast strain that replaces the yeast chromosomal telomere sequence with a mammalian telomere sequence was prepared. The mammalian telomere sequence was confirmed to be added to the yeast chromosome in the strain.

In summary, the present invention relates to:
(1) An artificial chromosome having a mammalian telomere sequence added to its ends.
(2) The artificial chromosome of (1), wherein said chromosome comprises an alphoid sequence.
(3) The artificial chromosome of (1) or (2), wherein said chromosome comprises a DNA replication origin and a centromere, both derived from an organism other than a mammal.
(4) The artificial chromosome of (3), wherein said organism other than a mammal is yeast.
(5) A hybrid telomerase capable of adding a mammalian telomere sequence to the ends of a chromosome, wherein said telomerase comprises a template RNA comprising a complementary sequence to a mammalian telomere sequence and a telomerase protein derived from an organism other than a mammal.
(6) The hybrid telomerase of (5), wherein said complementary sequence to a mammalian telomere sequence comprises 5'-CCCUAA-3'.
(7) The hybrid telomere of (5) or (6), wherein said organism other than a mammal is yeast.
(8) A method of producing a hybrid telomerase, which comprises producing a template RNA consisting of a complementary sequence to a mammalian telomere sequence in a host other than a mammal and allowing said template RNA to match with an endogenous telomerase protein of the host.
(9) The method of (8), wherein said host is yeast.
(10) The method of producing an artificial chromosome having a mammalian telomere sequence added to its ends, which comprises contacting any one of the hybrid telomerase of (5) to (7) to a chromosome.
(11) A eukaryotic cell capable of expressing a template RNA comprising a complementary sequence to a mammalian telomere sequence and capable of being the mammalian telomere sequence added to the ends of a chromosome in the cell.
(12) The eukaryotic cell of (11), wherein said cell is yeast.
(13) A method of producing an artificial chromosome having a mammalian telomere sequence added to its ends comprising introducing a chromosome into the cell of (11) or (12).

In the present invention, the term "chromosome" means a DNA molecule that exists stably as a single copy, independent of a host genome in the host, and is capable of replicating and separating following the host cell cycle. It generally contains a DNA replication origin, a centromere, and a telomere, and may be natural or artificial.

The artificial chromosome of the present invention means a chromosome containing at least a part not derived from the natural source.

The mammalian telomere sequence of the present invention means a sequence consisting primarily of repeated 5'-TTAGGG-3' sequences.

The method of constructing an artificial chromosome of the present invention is not particularly limited. For example, an artificial chromosome capable of functioning in mammalian cells can be constructed by inserting a DNA molecule containing a mammalian centromere sequence and a DNA replication origin into a vector and adding a mammalian telomere sequence to the end of the vector.

The vector used in this method is not particularly limited as long as a long-chain DNA molecule can be inserted into it. An example of such a vector is the YAC vector.

The method of adding a mammalian telomere sequence is not particularly limited. The method of expressing a mammalian telomerase in vivo and allowing it the function is preferable because the DNA molecule suffers less physical damage and gene manipulation in cells is enabled using homologous recombination techniques. In this method, the mammalian telomerase includes a hybrid telomerase in which only the RNA template among the telomerase constituents is modified into a mammalian type. A telomerase can be modified into a mammalian type structure by modifying the TLC1 gene encoding an RNA template of a yeast telomerase (Singer, M. S., and Gottschling, D. E., Science, 266:404–409 (1994)) by in vitro mutagenesis. This process replaces the DNA sequence "CACCACACCCACACAC (SEQ ID NO:1)" corresponding to the template region with the mammalian type DNA sequence "CACCTAACCG-TAACCC (SEQ ID NO:2)," expressing the mutant TLC1 gene in yeast. The resulting expression product is then allowed to associate with a yeast telomerase protein in vivo, thereby reconstituting a functional hybrid telomerase.

A desired gene that should function in the cell can be inserted into the artificial chromosome constructed by the above method and then introduced into a target cell. Any type of gene can be used. Since, theoretically, a DNA molecule of any length can be inserted into the artificial chromosome of the present invention, it is possible to use cDNA or a gene containing an expression regulatory region, such as a promoter or an enhancer, at the cis position located on the upstream side of the gene. Multiple genes can be used together. The artificial chromosome of the present invention can be applied to gene therapy in which expression of the gene must be strictly controlled, for example, gene therapy of a hemoglobin gene in thalassemia. More specifically, the artificial chromosome can be used to introduce a lengthy DNA molecule including a cis region necessary to control expression or to treat diseases caused by the lack of a long DNA region, such as chromosomal aberration, by supplementing a whole DNA region.

The artificial chromosome of the present invention can be introduced by microinjection or lipofection into an animal cell. Specifically, cell fusion is preferable because the artificial chromosome suffers less physical damage.

Any cell into which the artificial chromosome is to be introduced can be used as long as the artificial chromosome can function in the cell. For example, a mammalian cell from a primate other than a human can be used if an artificial chromosome has a mammalian telomere sequence at its ends and a mammalian alphoid sequence. A rodent such as a mouse may also be used.

BEST MODE FOR IMPLEMENTING THE INVENTION

EXAMPLE 1

Preparing YAC Clones Containing a Human Centromere Sequence and a Human DNA Replication Origin Clones containing a human alphoid sequence were selected from a CEPH artificial yeast chromosome library which was constructed by inserting a human genome into a YAC vector capable of incorporating a long-chain DNA molecule according to the method described in Hum. Mol. Genet. 3: 1245–1257 (1994).

As a result, five clones, 749H1, 818H1, 858F11, 882C10, and 831B6, possessed a human chromosome XXI alphoid sequence in the CEPH YAC library. Among these five clones, 858F11, which was 800 kb long and carried approximately 55 kb of the alphoid sequence (presumably including a human DNA replication origin), was used in the following experiment.

Since the pYAC4 vector used in the CEPH YAC library does not have markers for a mammalian cell, 858F11 clone-carrying yeast cells were transformed with a SalI/ClaI fragment of pYACNeoNot (provided by Howard Cooke, Medical Research Council (MRC) Human Genetics Unit, Edinburgh, UK). Neomycin-resistant gene neor and the SUP4 gene were then introduced into the 858F11 clone by homologous recombination. Southern hybridization was performed to confirm that an alphoid sequence was maintained in the YAC clone.

EXAMPLE 2

Preparing a Yeast Strain to Add a Mammalian Type Telomere Sequence (1) Humanizing a Template RNA of Yeast Telomerase

*S. cerevisiae* reportedly has a TLC1 gene encoding a template RNA of telomerase. First, a mutation was introduced into a template region of the TLC gene by in vitro mutagenesis to prepare a mutant TLC1 allele (hereinafter referred to as HTM3) which codes a human telomere sequence $(TTAGGG)_n$ instead of a yeast telomere sequence $(TG_{1-3})_n$. More specifically, a DNA sequence "CACCA-CACCCACACAC (SEQ ID NO:1)," a template region of the TLC1 gene encoding a template RNA of a yeast telomerase, was converted to a human telomere sequence "CACCTAACCCTAACCC (SEQ ID NO:2)." Moreover, the PvuII/XhoI cleavage site was introduced into the ends of the HTM3 gene using Tag primer.

(2) Over-Expression of HTM3 Using a GAL Promoter

A PvuII/XhoI fragment of HTM3 was inserted into the PvuII/XhoI site of pYES2 vector (hereinafter referred to as YEpUGH3). The pYES2 vector is an expression vector having a URA3 gene, a 2 µm plasmid replication orgin, and a GAL1 promoter. Yeast cells were transformed with YEpUG3, and HTM3 was over-expressed in the trasformants using a GAL1 promoter to obtain a mutant yeast strain (hereinafter referred to as Yeast Human Telomere Marker (YHTM)) having a functionally modified telomerase which synthesizes the human telomere sequence in vivo.

Southern hybridization was performed to confirm that the functionally modified telomerase actually functioned in YHTM, in other words, that the human telomere sequence was added to the ends of the yeast chromosome. Southern hybridization was conducted using oligo DNA $(CCCTAA)_4$ corresponding to the human telomere sequence as a probe in a hybridization solution containing 5×SSPE, 0.5% SDS, 0.5× Denhardt, and 20 µ/ml of h.s. DNA at 42° C. After the reaction, the filter was washed twice using a solution containing 1×SSRE and 0.1% SDS at room temperature for 10 minutes then washed again using a solution containing 0.1×SSPE and 0.1% SDS at room temperature for 10 minutes. After the washing, the obtained band was detected using a FUJI Image Analyzer and exposure for 20 hours. As a result, a band was detected at an expected position, confirming that the human telomere sequence was added to the yeast chromosome.

The ends of the yeast chromosome were then cloned, and the base sequences were determined. First, a yeast genome DNA was extracted, blunted by using T4 polymerase, then cleaved by restriction enzyme XhoI. After agarose gel electrophoresis, 0.9 to 1.1 kbp fragments were obtained from the gel. The fragment was then ligated with about a 2.9 kbp EcoRV/XhoI fragment derived from pBluscriptIISK (Toyobo), then the ligation product was used to transform *E. coli*. Colony hybridization was performed using a repetitive sequence of the yeast subtelomere region as a probe, positive clones were picked up, and the base sequences were determined using a standard method. As a result, about a 140 bp yeast telomere region was cloned. In this region, the human telomere sequence, CCCTAA, repeating two to five times, existed in tandem.

(3) Preparing a Yeast Strain in which TLC1 Gene is Replaced with HTM3

The TLC1 gene on the yeast chromosome was entirely replaced with HTM3 by homologous recombination in yeast to obtain a mutant yeast strain having in its genome a functionally modified telomerase gene that synthesizes a human telomere sequence. Cloning and determination of the sequence at the ends of YNH3 chromosome were conducted by using the method above. As a result, about a 190 bp yeast telomere region was cloned. In this region, a maximum of 18 repetitive telomere sequences of CCCTAA (109 bp) existed in tandem towards the end.

INDUSTRIAL APPLICABILITY

The present invention provides clones having a mammalian alphoid sequence and a yeast strain in which a mammalian telomere sequence can be added to the ends of the chromosome. The length of DNA to be introduced in the artificial chromosome of the present invention is theoretically unlimited. The artificial chromosome. exists stably as a single copy, independent of a host genome in a host, and undergoes DNA replication and chromosome separation following the cell cycle of the host. For example, the artificial chromosome of the present invention can be constructed to contain a human therapeutic gene with an expression control region, and expression of the introduced gene can be regulated under the physiological conditions.

What is claimed is:

1. A hybrid telomerase comprising (i) a *S. cerevisiae* yeast telomerase protein and (ii) a template RNA having a mammalian telomere sequence.

2. The hybrid telomerase of claim 1, wherein said template RNA comprises 5'-CCCUAA-3'.

3. A method of producing a hybrid telomerase, which comprises producing a template RNA having a mammalian telomere sequence in a yeast host and allowing said template RNA to assemble with an endogenous telomerase protein of said host.

4. The method of claim 3, wherein said template RNA comprises 5'-CCCUAA-3'.

5. A yeast cell comprising a telomeric template RNA having a mammalian telomere sequence, wherein said cell is capable of adding the complementary mammalian telomere sequence to the ends of a chromosome in the cell.

6. The cell of claim 5, wherein said template RNA comprises 5'-CCCUAA-3'.

* * * * *

SEQUENCE LISTING

<160> NUMBER OF SEQ ID NOS: 2

<210> SEQ ID NO 1
<211> LENGTH: 16
<212> TYPE: DNA
<213> ORGANISM: Saccharomyces cerevisiae

<400> SEQUENCE: 1
caccacaccc acacac                                                    16

<210> SEQ ID NO 2
<211> LENGTH: 16
<212> TYPE: DNA
<213> ORGANISM: Homo sapiens

<400> SEQUENCE: 2
cacctaaccc taaccc                                                    16